(12) United States Patent
Watanabe

(10) Patent No.: US 7,871,601 B2
(45) Date of Patent: Jan. 18, 2011

(54) HAIR COSMETIC COMPOSITIONS

(75) Inventor: Shunsuke Watanabe, Tokyo (JP)

(73) Assignee: Kao Corporation, Tokyo (JP)

( * ) Notice: Subject to any disclaimer, the term of this patent is extended or adjusted under 35 U.S.C. 154(b) by 1155 days.

(21) Appl. No.: 11/019,307

(22) Filed: Dec. 23, 2004

(65) Prior Publication Data

US 2005/0142091 A1 Jun. 30, 2005

(30) Foreign Application Priority Data

Dec. 25, 2003 (JP) .............................. 2003-431121

(51) Int. Cl.
*A61Q 5/12* (2006.01)
(52) U.S. Cl. ................................. 424/70.12; 424/70.11
(58) Field of Classification Search ........................ None
See application file for complete search history.

(56) References Cited

U.S. PATENT DOCUMENTS

| | | | |
|---|---|---|---|
| 4,954,335 A | | 9/1990 | Janchipraponvej |
| 5,609,861 A | | 3/1997 | Dubief et al. |
| 6,974,569 B2 * | | 12/2005 | Dunlop et al. ............. 424/70.1 |
| 6,979,439 B1 * | | 12/2005 | Sakai et al. ................ 424/70.8 |
| 2003/0198615 A1 | | 10/2003 | Wong et al. |
| 2004/0166084 A1 * | | 8/2004 | Sakai et al. .............. 424/70.27 |

FOREIGN PATENT DOCUMENTS

| | | | |
|---|---|---|---|
| EP | 0 027 730 | | 4/1981 |
| EP | 0 682 935 | | 11/1995 |
| EP | 0 682 935 A2 | | 11/1995 |
| EP | 1283030 | * | 2/2003 |
| EP | 1 366 755 | | 12/2003 |
| EP | 1 366 755 A1 | | 12/2003 |
| EP | 1 433 465 A2 | | 6/2004 |
| WO | WO 00/38621 | | 7/2000 |
| WO | WO 01/08654 | | 2/2001 |
| WO | WO 01/78670 A2 | | 10/2001 |
| WO | WO 01/78671 A2 | | 10/2001 |
| WO | WO 02/060408 A1 | | 8/2002 |
| WO | WO 03/037280 | | 5/2003 |
| WO | WO 03/037280 A1 | | 5/2003 |
| WO | WO 03/055457 A1 | | 7/2003 |

OTHER PUBLICATIONS

JP 2000-86452 (Mar. 2000) Abstract.
JP 10-7532 (Jan. 1988) Abstract.
JP 7-309723 (Nov. 19995) Abstract.
JP 2003-95842 (Apr. 2003) Abstract.
DE 29516226 (Feb. 1997) Abstract.
Database WPI, AN 2001-506321, XP-002325096, JP 2001-181156, Jul. 3, 2001.
JP 2003-321332 (Nov. 2003) Abstract.

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

A rinse-off type hair cosmetic composition containing the following ingredients: (A) from 1 to 10 wt % of a higher alcohol having from 12 to 28 carbon atoms, (B) a quaternary ammonium salt represented by the following formula (1) or a tertiary amine type compound represented by the following formula (2) or salt thereof,

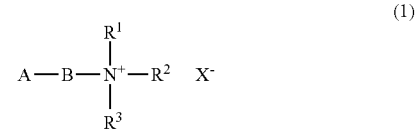

(1)

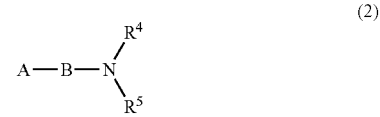

(2)

(C) from 15 to 70 wt % of a polyhydric alcohol, and (D) from 0.01 to 10 wt % of a dimethylpolysiloxane. The content ratio of the ingredient (A) to the ingredient (B) is from 1:1 to 10:1 in terms of molar ratio. As a method for preventing colored hair from fading, the hair cosmetic composition is used before or after shampooing the colored hair. The hair cosmetic composition can inhibit the bleeding of a colorant from colored hair upon shampooing, and is also excellent in the smoothness of the hair upon applying the composition and also upon rinsing it off.

5 Claims, No Drawings

HAIR COSMETIC COMPOSITIONS

FIELD OF THE INVENTION

This invention relates to rinse-off type hair cosmetic compositions containing a polyhydric alcohol and a cationic surfactant, which are used after or before shampooing colored hair to prevent the bleeding of the colorant from the colored hair during shampooing.

BACKGROUND OF THE INVENTION

Changing the hair color of a person by coloring can alter his or her impression by making him or her look young, cheerful and so forth. The colored hair is, however, accompanied by a problem that its color quickly fades through degradation or deterioration of the colorant by ultraviolet rays or oxidation or through bleeding of the colorant by repeated use of shampoo, hair treatment and/or the like.

To prevent such a fading, a UV absorber or antioxidant is generally incorporated in a hair cosmetic composition. Incorporation of such a UV absorber or the like only, however, is not sufficient to prevent this fading. For the purpose of preventing the bleeding of a colorant during shampooing, there have been proposed cleansing compositions with a silicone incorporated therein to coat the hair surface (U.S. Pat. No. 5,609,861 and U.S. patent application Publication No. 2003/0198615A). It is, however, difficult to effectively coat the interface between hair and water with a silicone or the like upon shampooing. With a view toward replenishing bled colorant, there have also been proposed shampoos and conditioners with the colorant incorporated therein directly (the international publication pamphlets of WO 03/055457, 01/78670 and 01/78671). These shampoos and conditioners, however, have not succeeded in fully satisfying consumers due to the reasons such as the hair color obtained after the shampooing becomes different from the original hair color imparted by the coloring or the colorant deposits in the skin or transfers to a towel, pillow case or the like.

SUMMARY OF THE INVENTION

In one aspect of the present invention, there is provided a rinse-off type hair cosmetic composition containing the following ingredients (A), (B), (C) and (D):

(A) from 1 to 10 wt % of a higher alcohol having from 12 to 28 carbon atoms, (B) a quaternary ammonium salt represented by the following formula (1):

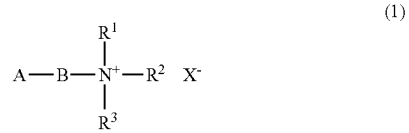

wherein A represents a hydrogen atom or a linear or branched, saturated or unsaturated amido, N-hydrocarbylcarbamoyl, acyloxy or hydrocarbyloxy group having from 12 to 28 carbon atoms in total, B represents a divalent, linear or branched, saturated or unsaturated hydrocarbon group having from to 22 carbon atoms, at least one of $R^1$, $R^2$ and $R^3$ represents a linear or branched alkyl or alkenyl group having from 1 to 24 carbon atoms in total and the remaining one or ones of $R^1$, $R^2$ and $R^3$ each independently represents an alkyl group having from 1 to 3 carbon atoms, and $X^-$ represents a halide ion or an organic anion; or a tertiary amine type compound or a salt thereof, said tertiary amine type compound being represented by the following formula (2):

wherein A and B have the same meanings as defined above, and $R^4$ and $R^5$ each independently represents an alkyl group having from 1 to 4 carbon atoms, (C) from 15 to 70 wt % of a polyhydric alcohol, and (D) from 0.01 to 10 wt % of a dimethylpolysiloxane;

wherein a content ratio of the ingredient (A) to the ingredient (B) is in the range of from 1:1 to 10:1 in terms of molar ratio.

In another aspect of the present invention, there is also provided a method for preventing colored hair from fading, which contains using the above-described hair cosmetic composition before or after shampooing the colored hair.

DETAILED DESCRIPTION OF THE INVENTION

This invention relates to rinse-off type hair cosmetic compositions, which are used after or before shampooing colored hair to prevent the bleeding of the colorant upon shampooing and are also excellent in the smoothness of the hair upon applying the composition and also upon rinsing it out.

The present inventors have found that a hair cosmetic composition, which meets the above-described requirements, can be obtained by using, in combination, a higher alcohol, an amine-type cationic surfactant, a polyhydric alcohol and a dimethylpolysiloxane in certain specific proportions.

The ingredient (A), i.e., the higher alcohol having from 12 to 28 carbon atoms imparts a smooth liquid property to the hair cosmetic composition and also a moisturized feel to the hair. As the higher alcohol, those having from 16 to 24 carbon atoms are preferred, with those having from 18 to 22 carbon atoms being more preferred. More specifically, linear, higher alkyl alcohols are preferred although linear or branched, saturated or unsaturated higher alcohols are usable.

Specific examples include cetyl alcohol, stearyl alcohol, arachyl alcohol, behenyl alcohol, 2-octyl dodecanol, 2-hexyldecyl alcohol, isostearyl alcohol, and carnaubyl alcohol (tetracosanol). Among these, cetyl alcohol, stearyl alcohol, behenyl alcohol and mixtures thereof are preferred.

As the higher alcohol (A), two or more of these higher alcohols can be used in combination. From the standpoint of providing wet hair with finger-combing ease and smoothness, providing the hair with a moisturized feel after drying and also providing the hair cosmetic composition with emulsion stability, the content of the higher alcohol (A) is required to be from 1 to 10 wt % based on the hair cosmetic composition, with a range of from 1.5 to 8 wt % being preferred, and a range of from 2 to 5 wt % being more preferred.

Examples of the quaternary ammonium salt represented by the formula (1) in the ingredient (B) include mono($C_{12-22}$ long-chain alkyl) quaternary ammonium salts, di ($C_{12-22}$ long-chain alkyl) quaternary ammonium salts, $C_{12-22}$ branched-chain alkyl quaternary ammonium salts, $C_{12-28}$-alkylamido-$C_{1-5}$-alkyl quaternary ammonium salts, N-$C_{12-28}$-hydrocarbylcalbamoyl-$C_{1-5}$-alkyl quaternary ammonium salts, $C_{12-28}$-acyloxy-$C_{1-5}$-alkyl quaternary ammonium salts, and $C_{12-28}$-hydrocarbyloxy-$C_{1-5}$-alkyl quaternary ammonium salts.

Examples of the mono ($C_{12-22}$ long-chain alkyl) quaternary ammonium salts include stearyltrimethylammonium chloride, myristyltrimethylammonium chloride, cetyltrimethylammonium chloride, arachyltrimethylammonium chloride, behenyltrimethylammonium chloride, lauryltrimethylammonium chloride, and N-stearyl-N,N,N-tri(polyoxyethylene)ammonium chloride (3 moles added in total). Examples of the di($C_{12-22}$ long-chain alkyl) quaternary ammonium salts include distearyldimethylammonium chloride, dioleyldimethylammonium chloride, dipalmitylmethylhydroxyethylammonium methosulfate, diisostearyldimethylammonium methosulfate, di[(2-dodecanoylamino)ethyl]dimethylammonium chloride, and di[(2-stearoylamino)propyl]dimethylammonium ethosulfate. Examples of the $C_{12-22}$ branched-chain alkyl quaternary ammonium salts include 2-decyltetradecyltrimethylammonium chloride, 2-dodecylhexadecyltrimethylammonium chloride, di-2-hexyldecyldimethylammonium chloride, and di-2-octyldodecyldimethylammonium chloride. Examples of the $C_{12-28}$-alkylamido-$C_{1-5}$-alkyl quaternary ammonium salts include stearamidopropyl quaternary ammonium salts. Examples of the N—$C_{12-28}$-hydrocarbyl-calbamoyl-$C_{1-5}$-alkyl quaternary ammonium salts include N-stearylcarbamoylpropyl quaternary ammonium salts. Examples of the $C_{12-28}$-acyloxy-$C_{1-5}$-alkyl quaternary ammonium salts include stearoyloxypropyl quaternary ammonium salts. Examples of the $C_{12-28}$-hydrocarbyloxy-$C_{1-5}$-alkyl quaternary ammonium salts include octadecyloxypropyltrimethylammonium chloride.

When A is other than a hydrogen atom in the formula (2) which represents the tertiary amine type compound in the ingredient (B), A can be an amido or hydrocarbyloxy group which has preferably from 14 to 22 carbon atoms in total, more preferably from 18 to 22 carbon atoms. More preferably, its hydrocarbon part may be saturated, with a saturated, linear hydrocarbon part being even more preferred. In this case, B may preferably be a trimethylene group. When A is a hydrogen atom, on the other hand, B may preferably be a hydrocarbon group having 18 to 22 carbon atoms, which may be preferably saturated, even more preferably saturated and linear. As examples of $R^4$ and $R^5$, methyl, ethyl, propyl, isopropyl, butyl and t-butyl can be mentioned. Among these, methyl and ethyl are preferred, with methyl being more preferred. As preferred examples of the tertiary amine type compound, N,N-dimethyloctadecyloxypropylamine and stearamidopropyldimethylamine can be mentioned.

The salt of the tertiary amine type compound can be formed by a neutralization reaction between the above-described tertiary amine type compound and an acidic amino acid, organic acid or inorganic acid. As examples of the acidic amino acid, glutamic acid and aspartic acid can be mentioned. Examples of the organic acid include carboxylic acids such as monocarboxylic acids, dicarboxylic acids, hydroxycarboxylic acids and polycarboxylic acids, alkylsulfuric acids, and alkylphosphoric acids. Among these, carboxylic acids, especially dicarboxylic acids and hydroxycarboxylic acids are preferred. Illustrative of the dicarboxylic acids are malonic acid, succinic acid, glutaric acid, adipic acid, maleic acid, fumaric acid and phthalic acid, and illustrative of the hydroxycarboxylic acids are glycolic acid, lactic acid, hydroxyacrylic acid, oxybutyric acid, glyceric acid, malic acid, tartaric acid and citric acid. Examples of the inorganic acid include phosphoric acid, sulfuric acid, nitric acid, and hydrochloric acid.

Among these, organic acids are preferred. More preferred are α-hydroxycarboxylic acids, with lactic acid and malic acid being even more preferred.

From the standpoint of the smoothness of the hair upon applying the composition and upon rinsing it off, the content ratio of the higher alcohol (A) to the quaternary ammonium or the tertiary amine type compound or its salt (B) is in the range of from 1:1 to 10:1 in terms of molar ratio. The molar ratio maybe preferably from 1.5:1 to 5:1, even more preferably from 2:1 to 4:1.

The polyhydric alcohol as the ingredient (C) means a water-soluble alcohol having two or more hydroxy groups. Illustrative are glycols having two hydroxy groups and condensation products thereof, glycerins having three hydroxy groups and condensation products thereof, and in addition, sugar alcohols. As these polyhydric alcohols are soluble in water, they are considered to effectively reduce the activity of water and as a result, to lower the swelling speed of the hair during shampooing and eventually to lower the bleeding speed of the colorant existing in the hair. Further, as the effect of reducing the bleeding becomes higher with the increase of the concentration of the polyhydric alcohol in the hair cosmetic composition, the incorporation of the polyhydric alcohol in an effective proportion is considered to effectively inhibit the bleeding of the coloration through regular shampooing. However, its incorporation in an excessively large proportion may impair the smoothness of the hair upon applying the composition or rinsing it off in some instances.

Specific examples of the polyhydric alcohol include glycols such as ethylene glycol, propylene glycol, 1,2-butylene glycol, 1,3-butylene glycol, 3-methyl-1,3-butylne glycol, dipropylene glycol and hexylene glycol, and condensation products thereof; glycerins and condensation products thereof; and sugar alcohols such as erythritol, pentitol and hexitol. More preferred are propylene glycol, glycerin and hexitol, with glycerin being even more preferred.

As the polyhydric alcohol (C), two or more of these polyhydric alcohols can be used in combination. From the standpoints of the inhibition of the bleeding of a colorant from the inside of the colored hair and the smoothness of the hair upon applying the composition and rinsing it off, the content of the polyhydric alcohol is required to be from 15 to 70 wt % based on the hair cosmetic composition of the present invention, with a range of from 20 to 65 wt % being preferred, and a range of from 25 to 60 wt % being more preferred.

As the ingredient (D), i.e., the dimethylpolysiloxane, one having a viscosity of from 50,000 to 50,000,000 mPa·s is preferred. More preferred is one having a viscosity of from 100,000 to 25,000,000 mPa·s, with one having a viscosity of from 500,000 to 10,000,000 mPa·s being even more preferred.

From the standpoint of providing the hair with smoothness and a light, silky feel after drying, the content of the dimethylpolysiloxane (D) may be preferably from 0.01 to 10 wt %, more preferably from 0.1 to 7 wt %, even more preferably from 0.1 to 5 wt %. From the standpoint of facilitating its incorporation, it is preferred to incorporate the dimethylpolysiloxane after diluting it with a cyclic silicone or with a dimethylpolysiloxane having a viscosity of from 10 to 10,000 $mm^2/s$.

In the hair cosmetic composition of the present invention, a water-soluble, nonionic polymer can be incorporated further as an ingredient (E). Specific examples of the water-soluble, nonionic polymer include polyoxyethylene glycol and hydroxyethylcellulose. As the polyoxyethylene glycol, one having a weight average molecular weight of from 100,000 to 10,000,000 is preferred, with one having a weight average molecular weight of from 250,000 to 7,500,000 being more preferred, and one having a weight average molecular weight of from 500,000 to 5,000,000 being even more preferred. As the hydroxyethylcellulose, on the other hand, one having a viscosity average molecular weight of from 50,000 to 5,000,000 is preferred, with one having a viscosity average molecular weight of from 100,000 to 2,500,000 being more preferred, and one having a viscosity average molecular weight of from 200,000 to 2,000,000 being even more preferred.

From the standpoint of providing the hair cosmetic composition of the present invention with spreadability upon applying it and also with good stability, the content of the water-soluble, nonionic polymer (E) may be preferably from 0.01 to 1 wt %, more preferably from 0.05 to 0.75 wt %, even more preferably from 0.1 to 0.5 wt %, all based on the hair cosmetic composition.

From the standpoint of prevention of the fading of the color by inhibiting the degradation or deterioration of the colorant existing inside the hair after coloring and also inhibition of the bleeding of the colorant by the deterioration or damages of the hair itself, an oil-soluble or water-soluble UV absorber can be also incorporated as an ingredient (F) in the hair cosmetic composition of the present invention. Examples of the oil-soluble UV absorber include those of the benzoic acid type, the anthranilic acid type, the salicylic acid type, the cinnamic acid type, and the benzophenone type. Examples include, as UV absorbers of the benzoic acid type, p-aminobenzoic acid (hereinafter abbreviated as "PABA"), ethyl p-aminobenzoate, glyceryl PABA, ethyldihydroxypropyl PABA, ethyl N-ethoxylate-PABA, ethyl N-dimethyl-PABA, butyl N-dimethyl-PABA, amyl N-dimethyl-PABA, and octyl dimethyl PABA; as a UV absorber of the anthranilic acid type, homomenthyl N-acetylanthranilate; as UV absorbers of the salicylic acid type, amyl salicylate, menthyl salicylate, homomenthyl salicylate, octyl salicylate, phenyl salicylate, benzyl salicylate, and p-isopropanolphenyl salicylate; as UV absorbers of the cinnamic acid type, octyl cinnamate, ethyl 4-isopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethylhexyl p-methoxycinnamate, 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl mono-2-ethylhexanoyl diparamethoxycinnamate; as UV absorbers of the benzophenone type, 2,4-dihydroxybenzophenone, 2,2'-dihydroxy-4-methoxybenzophenone, 2,2'-dihydroxy-4,4'-dihydroxybenzophenone, 2-hydroxy-4-methoxybenzophenone, 2-hydroxy-4-methoxy-4'-methylbenzophenone, 2-hydroxy-4-methoxybenzophenone, 4-phenylbenzophenone, 2-ethylhexyl-4'-phenylbenzophenone-2-carboxylate, 2-hydroxy-4-n-octoxybenzophenone, 4-hydroxy-3-carboxybenzophenone, and 4-t-butyl-4'-methoxydibenzoylmethane.

Examples of the water-soluble UV absorber include diethanolamine p-methoxycinnamate, sodium 2-hydroxy-4-methoxybenzophenone-5-sulfonate, tetrahydroxybenzophenone, methylherperidin, sodium 3-hydroxy-4-methoxycinnamate, sodium ferulate, 2-phenylbenzimidazole-5-sulfonic acid ("EUSOLEX™"; product of Merck & Co., Ltd.), and urocanic acid. Animal or plant extracts having UV absorbing effect can also be mentioned such as milfoil (*Achillea milleforium*), aloe, witch hazel, hamamelis, burdock, and sage. Among these, 2-ethoxyethyl p-methoxycinnamate and 2-hydroxy-4-methoxybenzophenone are preferred, with 2-ethoxyethyl p-methoxycinnamate being more preferred.

The content of the UV absorber (F) may be preferably from 0.01 to 1 wt %, more preferably from 0.02 to 0.8 wt %, even more preferably from 0.05 to 0.5 wt %, all based on the hair cosmetic composition of the present invention.

Similar to the incorporation of the UV absorber, an antioxidant may also be incorporated further as an ingredient (G) in the hair cosmetic composition of the present invention to inhibit the degradation of the colorant existing inside the hair, to prevent the bleeding and fading of the colorant and to inhibit the bleeding of the colorant as a result of damages to the hair. Examples of the antioxidant include vitamin E, vitamin E derivatives, vitamin C, cysteine, butylhydroxyanisole, butylhydroxytoluene, gallic acid, propyl gallate, erthorbic acid, erthorbate salts, sulfites, andhydrogensulfites. Among these, vitamin E and vitamin E derivatives are preferred. Illustrative of vitamin E derivatives are DL-α-tocopherol, DL-α-tocopherol acetate, and DL-α-tocopherol nicotinate.

The content of the antioxidant (G) may be preferably from 0.01 to 1 wt %, more preferably from 0.02 to 0.8 wt %, even more preferably from 0.05 to 0.5 wt %, all based on the hair cosmetic composition of the present invention.

The hair cosmetic composition of the present invention may additionally contain, as an emulsifier, one or more of nonionic surfactants such as polyoxyalkylene alkyl ethers, polyoxyalkylene fatty acid esters, polyoxyalkylene sorbitan fatty acid esters, polyoxyalkylene sorbitol fatty acid esters, polyoxyalkylene glycerol fatty acid esters, monoglycerides, and sorbitan fatty acid esters; and amphoteric surfactants such as acetic acid betaines, amidoaceticacidbetaines, sulfobetaines, amidosulfobetaines, imidazolium betaines, amino acids, amidoamines, phosphobetaines, alkylamine oxides, and amidoamine oxides. The content of such a surfactant may be preferably from 0.01 to 5 wt %, more preferably from 0.05 to 2.5 wt %, even more preferably from 0.1 to 1 wt %, all based on the hair cosmetic composition of the present invention.

In addition to the above-described ingredients, one or more of ingredients and additives which are commonly employed in hair cosmetic compositions can also be incorporated in the hair cosmetic composition of the present invention as needed depending upon the purpose of use. Such ingredients include, for example, viscosity increasing agents such as carboxyvinyl polymer; oil ingredients such as hydrocarbon oils, waxes and ester oils; conditioning agents such as cationized cellulose and cationized guar gum; modified silicones such as amino-modified silicones; preservatives such as paraben; antifungal and/or antimicrobial agents such as salicylic acid, triclosan and piroctone olamine; pH adjusters such as sodium hydroxide and potassium hydroxide; metal ion sequestering agents such as edetate salts and hydroxyethanediphosphonic acid; and animal- or plant-derived extracts and colorants.

No particular limitation is imposed on the form of the hair cosmetic composition of the present invention insofar as it is of such a wash-off type as being used after or before shampooing, and it can be formulated into a hair rinse, a hair conditioner, a hair treatment, or the like.

EXAMPLES

The present invention will hereinafter be described more specifically based on examples. It is, however, to be noted that the present invention shall not be limited to the following examples.

Examples 1-10 and Comparative Examples 1-3

The hair cosmetic compositions shown in Table 5 were each formulated, and by the testing methods to be described below, ranked for the bleeding of its colorant from hair, the smoothness of hair upon applying it, and the smoothness of hair upon rinsing it off.

(Bleeding of the Colorant from Hair)

(1) Preparation of Colored Tresses

Each tress was prepared by precisely weighing out 2.5 g of Caucasian light-brown hair of about 20 cm in length with no history of chemical treatments such as a permanent wave and binding the cuticle end with glue.

The bleach packs 1 and 2 shown in Table 1 were weighed out as much as 2.5 g each, combined into a uniform mixture, and then evenly applied on to the tress. After the tress was wrapped with a wrapping film and was then left at room temperature for 30 minutes, it was rinsed with running water and then dried by a dryer.

Subsequently, the hair color packs 1 and 2 shown in Table 2 were weighed out as much as 2.5 g each, combined into a uniform mixture, and then evenly applied onto the tress. The tress was wrapped with a wrapping film, and was then left at 30° C. for 30 minutes. While rinsing the tress with running water, the tress was shampooed once with the model shampoo (0.2 g) shown in Table 3, and the model conditioner (0.2 g) shown in Table 4 was applied to soak into the tress thoroughly. The tress was rinsed with water and then dried by a dryer.

TABLE 1

| Ingredients | wt % |
|---|---|
| Model Bleach Pack 1 | |
| Aqueous ammonia (28 wt %) | 10 |
| Ammonium hydrogencarbonate | 15 |
| Purified water | Balance |
| Model Bleach Pack 2 | |
| Hydrogen peroxide solution (35 wt %) | 15 |
| Cetanol | 2.5 |
| Strearyltrimethylammonium chloride (63 wt %) | 4 |
| Hydroxyquinoline sulfate | 0.05 |
| Phosphoric acid | Sufficient to adjust the pH to 3.5 |
| Fragrance | 0.5 |
| Purified water | Balance |

TABLE 2

| Ingredients | wt % |
|---|---|
| Model Hair Color Pack 1 | |
| Aqueous ammonia (28 wt %) | 5.0 |
| Monoethanolamine | 2.0 |
| Cetanol | 8.5 |
| 2-Methyl-5-hydroxyethylaminophenol | 0.4 |
| 4-Amino-2-hydroxytoluene | 0.3 |
| Paraaminophenol | 0.3 |
| Phenylenediamine | 0.3 |
| Resorcinol | 0.01 |
| POE(40) cetyl ether | 3.0 |
| POE(2) cetyl ether | 3.5 |
| Stearyltrimethylammonium chloride | 2.0 |
| Liquid paraffin | 0.5 |
| Sodium sulfite | 0.5 |
| Ascorbic acid | 0.5 |
| Tetrasodium edetate | 0.1 |
| Fragrance | 0.4 |
| Ammonium chloride | Sufficient to adjust the pH to 10 |
| Purified water | Balance |

TABLE 2-continued

| Ingredients | wt % |
|---|---|
| Model Hair Color Pack 2 | |
| Hydrogen peroxide solution (35 wt %) | 17.0 |
| Phosphoric acid | Sufficient to adjust the pH to 3.5 |
| Purified water | Balance |

TABLE 3

| Ingredients | wt % |
|---|---|
| Model Shampoo | |
| Sodium lauryl ether sulfate | 17.0 |
| Lauric diethanolamide | 2.0 |
| Fragrance | 0.5 |
| Citric acid | Sufficient to adjust the pH to 6 |
| Purified water | Balance |

TABLE 4

| Ingredients | wt % |
|---|---|
| Model Conditioner | |
| Behenyltrimethylammonium chloride | 0.8 |
| Stearyl alcohol | 2.5 |
| Fragrance | 0.3 |
| Purified water | Balance |

(2) Colorant Bleeding Test

The colored tress (2.5 g) was dipped in a beaker which contained water (70 g), and was then pulled out. While catching dripping water in the beaker, the model shampoo (0.2g) was applied. While making the tress extend straight with fingers, the colored tress was rubbed up and down 30 times with fingers over 30 seconds such that the colored tress was thoroughly covered with the model shampoo. With the model shampoo kept applied on the colored tress, the colored tress was dipped in the beaker and rinsed there for 30 seconds. Subsequently, water was squeezed off with fingers and caught in the beaker. Another beaker with water (70 g) contained therein was newly provided, the colored tress was rinsed there again for 30 seconds, and water was squeezed off likewise.

Next, one (0.2 g) of the hair cosmetic compositions shown in Table 5 was applied. While making the tress extend straight with fingers, the colored tress was rubbed up and down 30 times with fingers over 30 seconds such that the hair cosmetic composition thoroughly soaked into the colored tress. With the hair cosmetic composition kept applied on the colored tress, the colored tress was dipped in the beaker with water (70 g) contained therein, and was rinsed there for 30 seconds. Subsequently, water was squeezed off with fingers and caught in the beaker. A new beaker with water (70 g) contained therein was newly provided, the colored tress was rinsed there again for 30 seconds, water was squeezed off likewise, and the colored tress was dried with a dryer.

The above-described operations (the treatment with the model shampoo and the treatment with the hair cosmetic composition) were repeated 7 times so that 28 washing-containing beakers (14 beakers from the treatment with the model shampoo, and 14 beakers from the treatment with the hair cosmetic composition) were obtained. The washings in the thus-obtained 28 beakers were individually subjected to centrifugation at 3,000 rpm for 2 hours. With respect to each washing, its supernatant was collected and then filtered through a cellulose acetate filter (pore size: 0.45 μm). The absorbance of the filtrate at 475 nm was measured. The absorbance was measured with a 1 cm×1 cm cell by using a spectrophotometer "DU650" (trade name; manufactured by BECKMAN INSTRUMENTS, INC.). Employed as a measurement reference was a filtrate of a washing obtained by similar treatments on a tress which was similar to the above tress except that the coloring alone was not applied. The total value of 28 absorbance data so obtained was recorded as an index of the amount of bled colorant.

(Smoothness of Hair Upon Applying the Hair Cosmetic Compositions and Smoothness of Hair Upon Rinsing Them Off)

By five expert panelists, each tress was ranked for its smoothness upon applying one of the hair cosmetic compositions and upon rinsing it off. Firstly, the tress was shampooed with the model shampoo. The hair cosmetic composition was applied onto the tress, and was then rinsed off. The smoothness of the tress upon applying the hair cosmetic composition and that of the tress upon rinsing it off were ranked in accordance with the below-described standards. Concerning each of the properties, the average of scores of the five expert panelists was recorded as the results of the corresponding organoleptic ranking.

Ranking Standards
3: very good
2: good
1: cannot be said either
0: bad

Example 11

Hair Conditioner 1

|  | (wt %) |
|---|---|
| Stearyl alcohol | 3.0 |
| N,N-Dimethyloctadecyloxypropylamine | 2.0 |
| Dimethylpolysiloxane ("X-21-7633", trade name; product of Shin-Etsu Chemical Co., Ltd.) | 3.0 |
| Hydroxyethylcellulose ("SE400", trade name; product of Daicel Chemical Industries, Ltd.) | 0.2 |
| Lactic acid | 0.3 |
| Glycerin | 30.0 |
| Amino-modified silicone ("SS3588", trade name; Product of Nippon Unicar Co., Ltd.) | 0.5 |
| Tocopherol acetate | 0.2 |
| 2-Ethylhexyl paramethoxycinnamate | 0.1 |
| 2-Hydroxy-4-methoxybenzophenone | 0.1 |
| Fragrance | 0.1 |
| Sodium hydroxide | Sufficient to give pH 5 |
| Purified water | Balance |

Example 12

Hair Conditioner 2

|  | (wt %) |
|---|---|
| Behenyl alcohol | 3.0 |
| Behenyltrimonium chloride | 1.0 |
| Highly-polymerized polyethylene glycol | 0.2 |

TABLE 5

| Ingredients (wt %) | Examples | | | | | | | | | | Comparative Examples | | |
|---|---|---|---|---|---|---|---|---|---|---|---|---|---|
|  | 1 | 2 | 3 | 4 | 5 | 6 | 7 | 8 | 9 | 10 | 1 | 2 | 3 |
| Stearyl alcohol | 3 | 3 | 3 | 3 | 3 | 3 | 3 | 3 | 3 | 3 | 3 | 3 | 3 |
| N,N-Dimethyloctadecyloxy-propyl amine | 1.5 | 2 | 2 | 2 | 2 | 2 | 2 | 2 | 1.5 | 1.5 | 2 | 2 | 2 |
| Dimethylpolysiloxane* | 3 | 3 | 3 | 3 | 3 | 3 | 3 | 3 | 3 | 3 | 3 | 3 | 3 |
| Highly-polymerized polyethylene glycol** | 0.25 | 0.25 | 0.25 | 0.25 | 0.25 | 0.25 | 0.25 | 0.25 | 0.25 | 0.25 | 0.25 | 0.25 | 0.25 |
| Lactic acid | 0.38 | 0.33 | 0.33 | 0.33 | 0.33 | 0.33 | 0.33 | 0.33 | 0.38 | 0.38 | 0.33 | 0.33 | 0.33 |
| Glycerin | 15 | 20 | 25 | 30 | 50 | 60 | 65 | 70 | — | — | — | 10 | 75 |
| Propylene glycol | — | — | — | — | — | — | — | — | 30 | — | — | — | — |
| Sorbitol | — | — | — | — | — | — | — | — | — | 30 | — | — | — |
| Fragrance | 0.4 | 0.4 | 0.4 | 0.4 | 0.4 | 0.4 | 0.4 | 0.4 | 0.4 | 0.4 | 0.4 | 0.4 | 0.4 |
| Purified water | Bal | Bal | Bal | Bal | Bal | Bal | Bal | Bal | Bal | Bal | Bal | Bal | Bal |
| Ingredient (A)/Ingredient (B) (mol/mol) | 2.63 | 2.0 | 2.0 | 2.0 | 2.0 | 2.0 | 2.0 | 2.0 | 2.63 | 2.63 | 2.0 | 2.0 | 2.0 |
| Bleeding of colorant from hair | 1.24 | 1.20 | 1.01 | 0.93 | 0.88 | 0.80 | 0.82 | 0.79 | 1.10 | 0.99 | 1.45 | 1.40 | 0.73 |
| Smoothness of hair upon applying hair cosmetic composition | 2.5 | 2.6 | 2.4 | 2.4 | 2.4 | 2.4 | 2.0 | 2.0 | 2.2 | 2.4 | 2.4 | 2.6 | 1.6 |
| Smoothness of hair upon rinsing | 2.4 | 2.6 | 2.6 | 2.4 | 2.6 | 2.4 | 2.4 | 2.2 | 2.2 | 2.4 | 2.6 | 2.4 | 1.8 |

*"DC 1501" (trade name; product of Dow Corning Corporation)
**"POLYOX ™ WSR N-60K" (product of The Dow Chemical Company.)

-continued

|  | (wt %) |
|---|---|
| ("POLYOX ™ WSR N-60K"; product of The Dow Chemical Company) | |
| Propylene glycol | 40.0 |
| Dimethylpolysiloxane ("DC 1501", trade name; product of Dow Corning Corporation) | 5.0 |
| Amino-modified silicone emulsion ("SM8704C", trade name; product of Dow Corning Toray Silicone Co., Ltd.) | 0.5 |
| Tocopherol acetate | 0.2 |
| 2-Ethylhexyl paramethoxycinnamate | 0.1 |
| 2-Hydroxy-4-methoxybenzophenone | 0.1 |
| Fragrance | 0.1 |
| Sodium hydroxide | Sufficient to give pH 5 |
| Purified water | Balance |

The invention claimed is:

1. A rinse-off hair cosmetic composition comprising the following ingredients (A), (B), (C), (D) and (E):
   (A) from 2-5 wt % of stearyl alcohol N,N-dimethyloctadecyloxy propylamine,
   (C) from 25-60 wt % of glycerine,
   (D) from 0.01-5 wt % of dimethylpolysiloxane having a viscosity from 10-10,000 mm$^2$/sec,
   (E) from 0.01-5 wt % of a polyoxyethylene glycol having a weight average molecular weight from 500,000 to 5,000,000; and water
   wherein a content ratio of said ingredient (A) to said ingredient (B) in the range of from 2:1 to 4:1 in terms of molar ratio.

2. The hair cosmetic composition according to claim 1, further comprising, as an ingredient (F), from 0.01 to 1 wt % of a UV absorber.

3. The hair cosmetic composition according to claim 1, further comprising, as an ingredient (G), from 0.01 to 1 wt % of an antioxidant.

4. A method for reducing colored hair from fading, which comprises using a hair cosmetic composition as defined in claim 1 before or after shampooing said colored hair.

5. The hair cosmetic composition according to claim 1, wherein said glycerine reduces the activity of water.

* * * * *

UNITED STATES PATENT AND TRADEMARK OFFICE
CERTIFICATE OF CORRECTION

| | | |
|---|---|---|
| PATENT NO. | : 7,871,601 B2 | Page 1 of 1 |
| APPLICATION NO. | : 11/019307 | |
| DATED | : January 18, 2011 | |
| INVENTOR(S) | : Shunsuke Watanabe | |

It is certified that error appears in the above-identified patent and that said Letters Patent is hereby corrected as shown below:

Col. 11, Claim 1, lines 3-4,

Replace "stearyl alcohol N,N-dimethyloctadecyloxy propylamine,"

with --stearyl alcohol, (B) N,N-dimethyloctadecyloxypropyl amine,--

Col. 12, line 2,

Replace "0.01-5 wt%" with --0.1-5 wt %--

Col. 12, line 4,

Replace "0.01-5 wt %" with --0.1-0.5 wt %--

Signed and Sealed this

Seventeenth Day of May, 2011

David J. Kappos
*Director of the United States Patent and Trademark Office*